United States Patent
Lorenzo et al.

(10) Patent No.: US 10,182,927 B2
(45) Date of Patent: Jan. 22, 2019

(54) EXPANSION RING FOR A BRAIDED STENT

(71) Applicant: DePuy Synthes Products, Inc., Raynham, MA (US)

(72) Inventors: Juan Lorenzo, Newton, MA (US); Robert Slazas, Palmetto Bay, FL (US); Ramin Tehrani, Pompano Beach, FL (US); Pedro Pedroso, Parkland, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 15/299,918

(22) Filed: Oct. 21, 2016

(65) Prior Publication Data

US 2018/0110636 A1    Apr. 26, 2018

(51) Int. Cl.
*A61F 2/852* (2013.01)
*A61F 2/89* (2013.01)
(Continued)

(52) U.S. Cl.
CPC ............... *A61F 2/89* (2013.01); *A61F 2/844* (2013.01); *A61F 2/848* (2013.01); *A61F 2/852* (2013.01); *A61F 2/90* (2013.01); *A61F 2/86* (2013.01); *A61F 2/93* (2013.01); *A61F 2002/8486* (2013.01); *A61F 2220/0025* (2013.01); *A61F 2220/0033* (2013.01); *A61F 2220/0041* (2013.01); *A61F 2220/0091* (2013.01); *A61F 2250/001* (2013.01)

(58) Field of Classification Search
CPC .............................................. A61F 2200/0025
See application file for complete search history.

(56) References Cited

U.S. PATENT DOCUMENTS

| | | | | |
|---|---|---|---|---|
| 4,610,688 A | * | 9/1986 | Silvestrini | A61F 2/06 623/1.53 |
| 5,064,435 A | * | 11/1991 | Porter | A61F 2/90 606/151 |

(Continued)

FOREIGN PATENT DOCUMENTS

| | | |
|---|---|---|
| EP | 2777638 A1 | 9/2014 |
| WO | 2013151793 A1 | 10/2013 |

OTHER PUBLICATIONS

Exptended European Search Report dated Feb. 23, 2018 during the prosecution of European Patent Application No. 17197578.2.

*Primary Examiner* — Jacqueline Woznicki

(74) *Attorney, Agent, or Firm* — Troutman Sanders LLP

(57) ABSTRACT

A braided stent system includes a stent body having a lumen formed by a plurality of braided members with interstices formed therebetween and a first expansion ring connected to the lumen of the stent body. The first expansion ring may include a frame defined by a plurality of interconnected support assemblies that are selectively positioned to impart an outwardly expanding radial force to the stent body, each support assembly can include a plurality of legs joined at a first intersection and connected to one of the other interconnected support assemblies at a second intersection opposite the first intersection. Each support assembly can include a claw portion mechanically connected to one or more of the interstices of the stent body so that the frame imparts an outward radial expansion force of the stent to facilitate use and delivery of the stent.

10 Claims, 12 Drawing Sheets

(51) Int. Cl.
*A61F 2/848* (2013.01)
*A61F 2/90* (2013.01)
*A61F 2/844* (2013.01)
*A61F 2/86* (2013.01)
*A61F 2/93* (2013.01)

(56) References Cited

U.S. PATENT DOCUMENTS

| | | | | |
|---|---|---|---|---|
| 5,330,500 | A * | 7/1994 | Song | A61F 2/90 606/198 |
| 5,476,508 | A * | 12/1995 | Amstrup | A61F 2/90 606/191 |
| 5,549,662 | A * | 8/1996 | Fordenbacher | A61F 2/93 606/198 |
| 5,601,593 | A * | 2/1997 | Freitag | A61F 2/90 606/191 |
| 5,609,627 | A * | 3/1997 | Goicoechea | A61F 2/07 128/898 |
| 5,776,161 | A * | 7/1998 | Globerman | A61F 2/90 606/192 |
| 5,817,126 | A * | 10/1998 | Imran | A61F 2/90 623/1.15 |
| 5,849,037 | A * | 12/1998 | Frid | A61F 2/90 606/195 |
| 5,899,935 | A * | 5/1999 | Ding | A61F 2/90 623/1.53 |
| 5,916,264 | A * | 6/1999 | Von Oepen | A61F 2/07 623/1.15 |
| 6,033,436 | A * | 3/2000 | Steinke | A61F 2/93 606/194 |
| 6,051,020 | A * | 4/2000 | Goicoechea | A61F 2/82 623/1.35 |
| 6,165,213 | A * | 12/2000 | Goicoechea | A61F 2/07 623/1.11 |
| 6,176,875 | B1 * | 1/2001 | Lenker | A61F 2/07 623/1.49 |
| 6,488,702 | B1 * | 12/2002 | Besselink | A61B 17/11 606/155 |
| 6,673,107 | B1 * | 1/2004 | Brandt | A61F 2/856 623/1.35 |
| 6,770,089 | B1 * | 8/2004 | Hong | A61F 2/91 623/1.15 |
| 9,427,343 | B2 * | 8/2016 | Bogert | A61F 2/07 |
| 9,713,523 | B2 * | 7/2017 | Zacharias | A61F 2/07 |
| 2001/0025195 | A1 * | 9/2001 | Shaolian | A61F 2/07 623/1.13 |
| 2002/0151953 | A1 * | 10/2002 | Chobotov | A61F 2/954 623/1.11 |
| 2002/0151956 | A1 * | 10/2002 | Chobotov | A61F 2/07 623/1.12 |
| 2002/0188344 | A1 * | 12/2002 | Bolea | A61F 2/90 623/1.11 |
| 2005/0033406 | A1 * | 2/2005 | Barnhart | A61F 2/07 623/1.13 |
| 2006/0064156 | A1 | 3/2006 | Thistle | |
| 2007/0005127 | A1 * | 1/2007 | Boekstegers | A61F 2/2493 623/1.16 |
| 2007/0043432 | A1 * | 2/2007 | Perouse | A61F 2/07 623/1.36 |
| 2007/0100427 | A1 * | 5/2007 | Perouse | A61F 2/07 623/1.11 |
| 2007/0167955 | A1 * | 7/2007 | Arnault De La Menardiere | A61F 2/07 606/108 |
| 2007/0233223 | A1 * | 10/2007 | Styrc | A61F 2/2439 623/1.11 |
| 2008/0221670 | A1 * | 9/2008 | Clerc | A61F 2/07 623/1.34 |
| 2009/0082844 | A1 * | 3/2009 | Zacharias | A61F 2/07 623/1.13 |
| 2009/0082845 | A1 * | 3/2009 | Chobotov | A61F 2/07 623/1.13 |
| 2009/0082847 | A1 * | 3/2009 | Zacharias | A61F 2/82 623/1.15 |
| 2009/0198315 | A1 * | 8/2009 | Boudjemline | A61F 2/2418 623/1.2 |
| 2009/0248133 | A1 * | 10/2009 | Bloom | A61F 2/2418 623/1.15 |
| 2009/0287145 | A1 * | 11/2009 | Cragg | A61F 2/07 604/96.01 |
| 2009/0326640 | A1 * | 12/2009 | Yoshimura | A61F 2/07 623/1.15 |
| 2010/0161028 | A1 * | 6/2010 | Chuter | A61F 2/07 623/1.13 |
| 2010/0292777 | A1 * | 11/2010 | Meyer | A61F 2/915 623/1.16 |
| 2010/0324651 | A1 * | 12/2010 | Holzer | A61F 2/90 623/1.15 |
| 2011/0184508 | A2 * | 7/2011 | Burmeister | A61F 2/844 623/1.19 |
| 2011/0264186 | A1 * | 10/2011 | Berglung | A61F 2/86 623/1.11 |
| 2012/0041538 | A1 * | 2/2012 | White | A61F 2/885 623/1.12 |
| 2012/0191176 | A1 * | 7/2012 | Nagl | A61F 2/848 623/1.15 |
| 2013/0041454 | A1 * | 2/2013 | Dobson | A61F 2/82 623/1.15 |
| 2013/0123901 | A1 * | 5/2013 | Connor | A61F 2/86 623/1.15 |
| 2013/0144375 | A1 * | 6/2013 | Giasolli | A61F 2/82 623/1.16 |
| 2013/0345739 | A1 * | 12/2013 | Brady | A61B 17/221 606/200 |
| 2014/0277376 | A1 * | 9/2014 | Lorenzo | A61F 2/82 623/1.16 |
| 2014/0336741 | A1 * | 11/2014 | Connor | A61F 2/958 623/1.11 |
| 2015/0265400 | A1 * | 9/2015 | Eidenschink | A61B 17/0644 623/2.18 |
| 2015/0320556 | A1 * | 11/2015 | Levi | A61F 2/2427 623/2.11 |
| 2016/0038280 | A1 * | 2/2016 | Morriss | A61F 2/2436 623/2.18 |
| 2017/0281375 | A1 * | 10/2017 | Longo | A61F 2/848 |
| 2017/0290686 | A1 * | 10/2017 | Sirhan | A61F 2/89 |

* cited by examiner

A-A

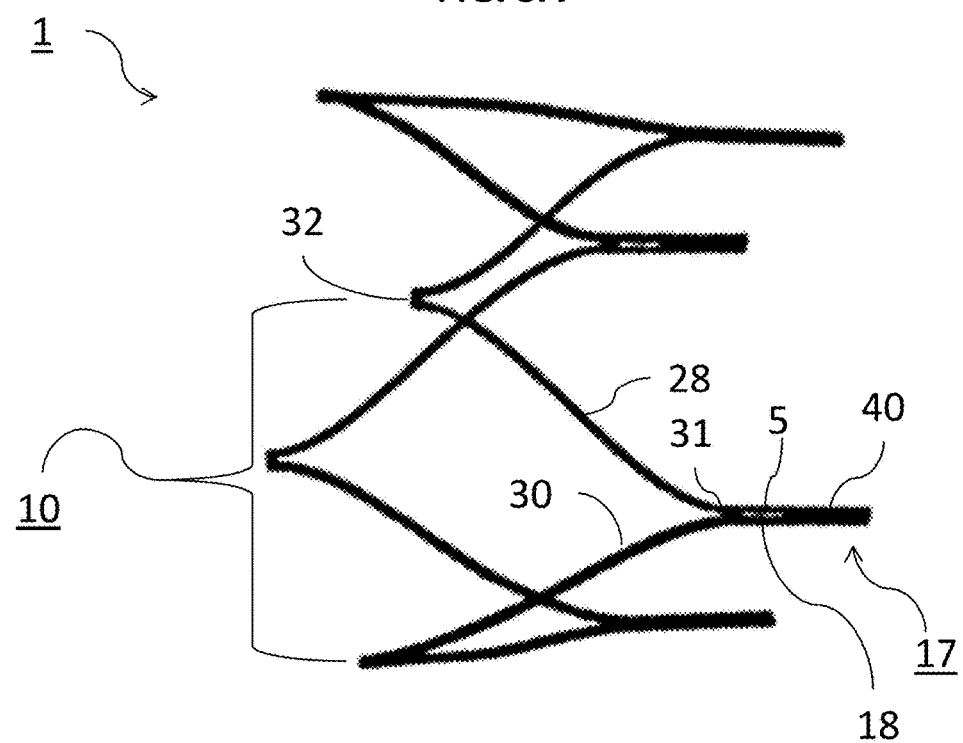

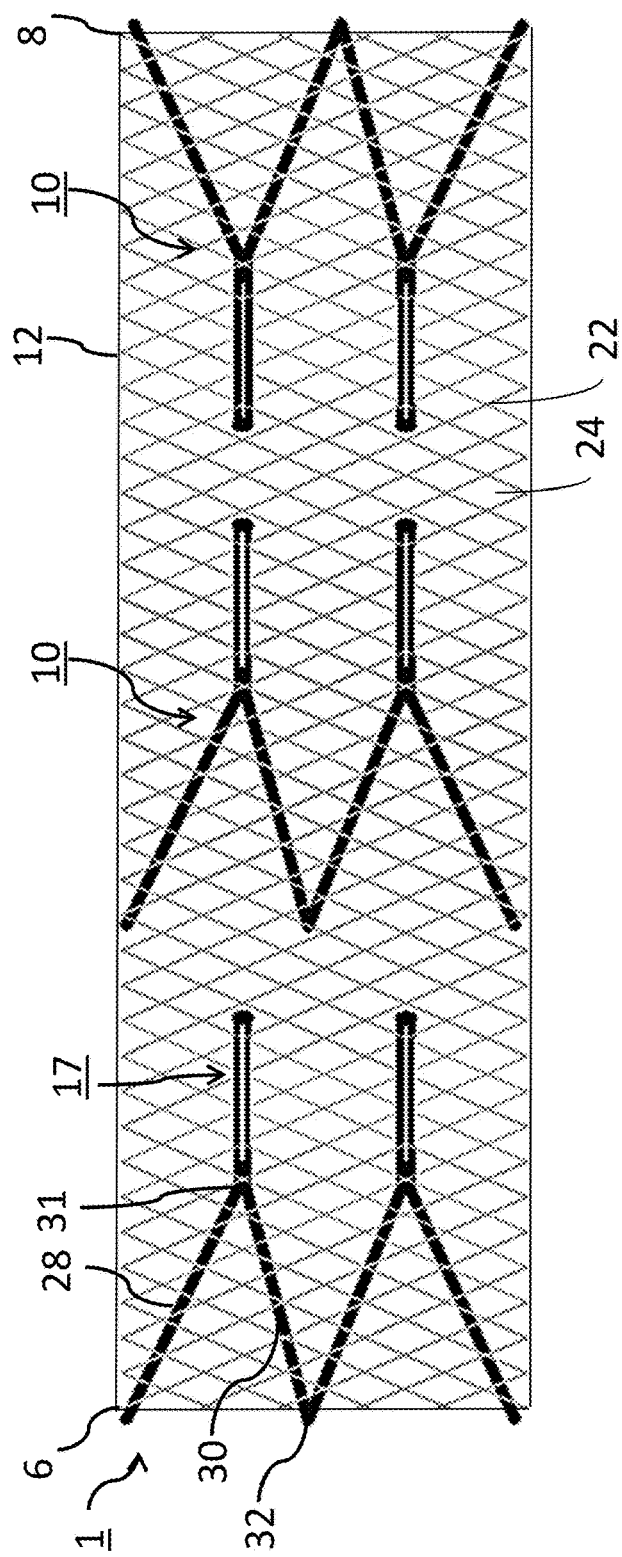

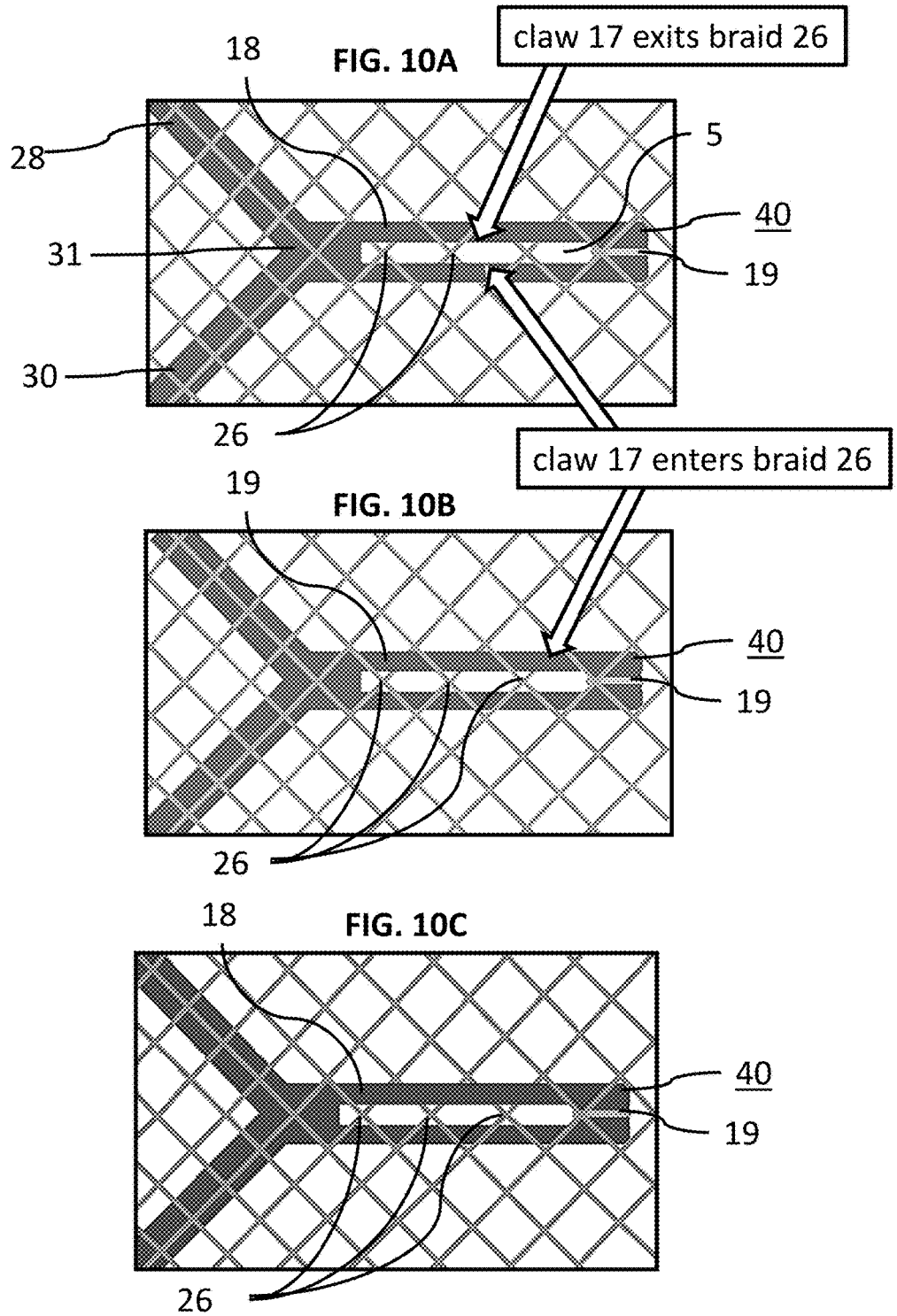

EXPANSION RING FOR A BRAIDED STENT

FIELD

The present disclosure relates generally to treatment of certain defects in a vasculature of a patient and more particularly, to self-expanding braided stents to a treatment site in a vasculature of a patient.

BACKGROUND

Stents are understood as tubular reinforcements that can be inserted into a blood vessel to provide an open path within the blood vessel. Stents have been widely used in intravascular angioplasty treatment of occluded cardiac arteries, wherein the stent may be inserted after an angioplasty procedure to prevent restenosis of the artery. Stents are often deployed by use of delivery devices which cause the stent to open with the objective of reinforcing the artery wall and provide a clear through-path in the artery thereby preventing restenosis.

However, the weakness and non-linear nature of the neurovasculature limits the applicability of such stents in procedures, for example, in repairing neurovascular defects. Furthermore, known delivery methods are less useful in vasoocclusive surgery, particularly when tiny vessels, such as those found in the brain, are to be treated. Accordingly, a need exists for a stent that can be used with delivery techniques in vasoocclusive treatment of neurovascular defects that provides selective reinforcement in the vicinity of the neurovascular defect. A need also exist for a stent that reduces trauma or risk of rupture to the blood vessel. It is with respect to these and other considerations that the various embodiments described below are presented.

SUMMARY

In some aspects, the present disclosure relates to a braided stent system for delivery into a blood vessel is disclosed. They system may include a stent body having a lumen formed by a plurality of braided members with interstices formed therebetween. An expansion ring may be mechanically connected to the lumen of the stent body and be operable to maintain the expansion ring in an opened state by having its frame impart an outwardly expanding radial force to the stent body. The frame may include plurality of legs joined at a first intersection and a claw portion mechanically connected to one or more of the interstices of the stent body. The claw portion may mechanically connect the expansion ring to one or more of the interstices by extending away from the first intersection through a plurality of the interstices and terminating at a locking mechanism opposite the first intersection.

In certain embodiments, the claw portion may include at least two aligned elongate members that extend between the first intersection and the locking mechanism to form a void therebetween. One or a plurality of the interstices may pass through the void as the claw portion mechanically connects the expansion ring to the stent body. The plurality of legs of the frame may also be bowed and/or oriented in a non-linear configuration causing the frame to be resistant to compression so that the braided stent system is self-expanding. The legs may be rotatable, pivotable, and/or twistable a predetermined amount about the first intersection.

In other embodiments, a braided stent system is disclosed having a stent body having a lumen formed by a plurality of braided members with interstices formed therebetween and a first expansion ring connected to the lumen of the stent body. The first expansion ring may include a frame defined by a plurality of interconnected support assemblies that are selectively positioned to impart an outwardly expanding radial force to the stent body, each support assembly can include a plurality of legs joined at a first intersection and connected to one of the other interconnected support assemblies at a second intersection opposite the first intersection. Each support assembly can also include a claw portion mechanically connected to one or more of the interstices of the stent body.

The plurality of legs of the frame may be bowed and/or oriented in a non-linear configuration causing the frame to be resistant to compression so that the braided stent system is self-expanding. The legs may be rotatable, pivotable, and/or twistable a predetermined amount about the first intersection.

The claw portion may also mechanically connect the expansion ring to inner and outer portions of the lumen by extending away from the first intersection, being interlaced through at least two of the interstices, and being terminated at a locking mechanism opposite the intersections. The locking mechanism may include a T-shaped end or outwardly extending hooked members operable to fixedly connect to the interstices of the stent body. The solution is not so limited, however, and at least one of the claw portions may include a plurality of aligned elongate members that extend between respective first intersections and locking mechanisms to form a void through which the plurality of interstices can pass.

In an example embodiment, one or a plurality of braided pairs of the braided members can pass through the void. The locking mechanism may also fixedly connect the expansion ring to the stent body by joining ends of the aligned elongate members opposite the first intersection through welding, soldering, crimping, or an adhesive bond. The solution is not so limiting, however, and the locking mechanism may fixedly connect the expansion ring to the stent body by joining ends of the aligned elongate members opposite the first intersection through a fastener such as a metallic band and/or ring. Additionally, at least one of the first and/or second intersections can form a V-shape, a U-shape, or an elliptical curve.

In another example embodiment, the stent body can include a proximal end, a distal end, and a central portion disposed therebetween. The first expansion ring can be disposed on or adjacent the distal or proximal ends of the stent body with the second intersections of the interconnected support assemblies being joined at or adjacent the respective distal or proximal ends. One or more additional expansion rings can also be connected to the lumen along or in connection with the central portion of the stent body and/or the opposing, distal or proximal end of the stent body.

A method of deploying a braided stent body into a vessel is also disclosed, the method comprising the following steps: assembling a plurality of expansion rings to a lumen of the braided stent body, the lumen of the braided stent body being formed by a plurality of braided members with interstices formed therebetween; selectively positioning each expansion ring with the braided stent body; each expansion ring imparting an outwardly expanding radial force thereby maintaining the lumen of the braided stent body in an opened position, each expansion ring comprising: a frame defined by a plurality of interconnected support assemblies comprising a plurality of legs joined at a first intersection and connected to one of the other interconnected support assemblies at a second intersection opposite the first intersection, the legs being twistable about the first and second intersections; and a claw portion disposed opposite the first and second intersections; mechanically connecting the claw portion of each ring to an inner portion of the stent body by interlacing a first elongate member extended between the respective claw portion and the respective first intersection of the expansion ring with one or more of the interstices and terminated at a locking mechanism opposite the intersections; and translating the braided members in the vessel independently from each expansion ring.

Since at least one of the claw portions can include a second alignment member substantially aligned with the first elongate member and extended between respective first intersections and locking mechanisms, the method can also include forming a void between the first and second elongate members and respective first intersections and locking mechanisms; and passing one or a plurality of braided pairs of the braided members through the void. The method may also include fixedly connecting the expansion ring to the stent body by joining ends of the first and second elongate members opposite the first intersection through welding, soldering, crimping, an adhesive bond, and/or a fastener.

Other aspects and features of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 5A is a perspective of an exemplary expansion ring with multiple claws prior to being assembled with a tubular braided stent body.

FIG. 8 depicts a side plan view of exemplary expansion rings having multiple claws when assembled at proximal and distal ends of a tubular braided stent body as well as at least one expansion ring placed along the body between the distal and proximal ends.

FIG. 10A depicts a close up side plan view of an exemplary expansion ring assembled with a tubular stent body depicting certain features of the expansion ring entering and exiting braids of the tubular stent body in a first arrangement.

FIG. 10B depicts a close up side plan view of an exemplary expansion ring assembled with a tubular stent body depicting certain features of the expansion ring entering and exiting braids of the tubular stent body in a second arrangement.

FIG. 10C depicts a close up side plan view of an exemplary expansion ring assembled with a tubular stent body depicting certain features of the expansion ring entering and exiting braids of the tubular stent body in a third arrangement.

DETAILED DESCRIPTION

Figure 1:
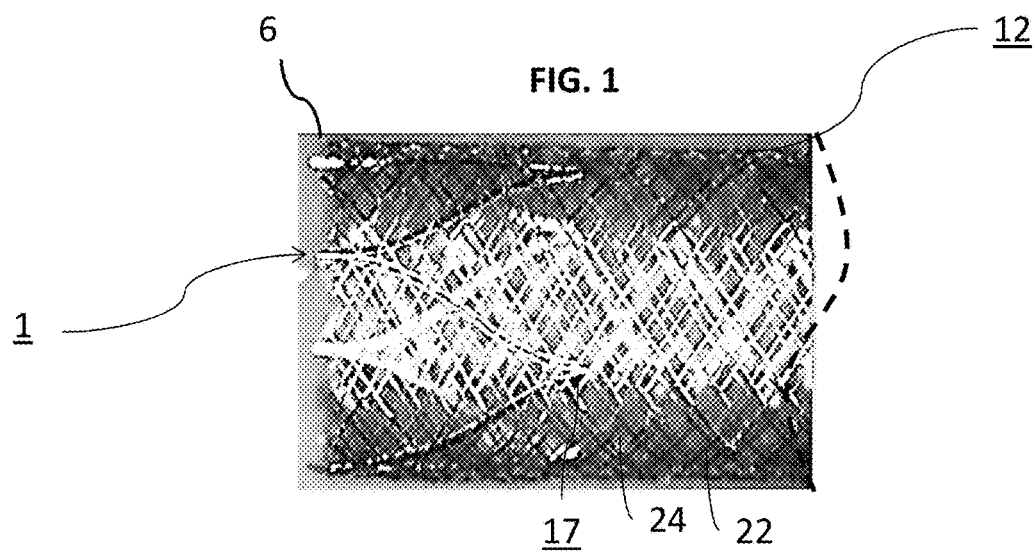
FIG. 1 depicts a side plan view of one embodiment of the herein disclosed expansion ring assembled at an end of a tubular braided stent body.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" may be vasculature of a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

Braided stents may be formed from a plurality of elongate members (e.g. metal wires, polymeric fibers, or strands of material) and these members can be very useful in treatment of neurovascular defects. However, when such braided members are intended to be self-expanding in a lumen of a stent body, known manners of activation of the initially expanding end struggle to adequately, reliably, and fully open so that the initially expanding end can be used as an anchor point. Moreover, braided stents have been known to exhibit high internal friction that resists the inherent radial expansion force of the self-expanding braided stent when being deployed to an opened state. More specifically, the relatively high internal friction can render it difficult to open the initially expanding end of the stent which results in deficiencies in anchoring and deployment. This is particularly true for braided stents delivered to the desired vessel location through use of a delivery sheath, microcatheter, or the like, since in a closed state (e.g. compressed or crimped) the stent body typically exhibits friction between the braided members and the delivery sheath or microcatheter.

In practice, braided stents can be delivered to a particular vessel by advancing a blunt surface against a proximal end of the braided stent causing the braided stent to axially compress and expand radially. This expansion within the delivery sheath or microcatheter can result in an increased normal force being applied to the inner surface of the delivery sheath, microcatheter, or the like thereby also increasing friction caused by the braided stent.

Known solutions to these issues have depended on factors such as material, size, cell design, internal friction, and extra manipulation by the end-user to reliably, quickly and adequately open the braided stents. In turn, success of the braided stent relied heavily on end-user accuracy in delivery which unnecessarily increases risk of injury to the patient.

Moreover, such braided, self-expanding stents can be difficult to recapture after being delivered and/or deployed. It is to be understood that a "self-expanding" stent is a stent wherein the particular stent fully deploys upon emerging through a delivery device such as a sheath, microcatheter, or the like. In this respect, when a self-expanding stent body emerges, unrestrained outside of the respective delivery device, the self-expanding braided stent should expand and be deployed in the vasculature. However, due to the referenced radial forces and friction, stent deployment and recapture following deployment is difficult.

The herein disclosed expansion ring 1 resolves these and other issues by providing a secure, mechanical attachment between ring 1 and the corresponding, braided stent body 12 that increases an outwardly extending radial expansion force of an initial proximal deployment end 6 of body 12, an opposing distal end 8 of body 12, and/or a central portion defined between each end 6 and 8. Instead, ring 1 includes one or a plurality of interconnected support assemblies 10 that collectively cause the ring to fully anchor itself with the lumen 20 of body 12 by mechanically securing a claw 17 of each assembly 10 to be interlaced with the braided, elongate members 22 of body 12. As a result, the total internal friction of body 12 is reduced and members 22 can move body 12 independent from ring 1 as discussed more particularly below. Assembling one or more multiple rings 1 with body 12 results in relatively easy delivery without the need for accurate positioning of ring 1 with body 12. In turn, deployment of the body 12 within the vasculature is more reliable with reduced risk of injury for the end-user.

Figure 2:
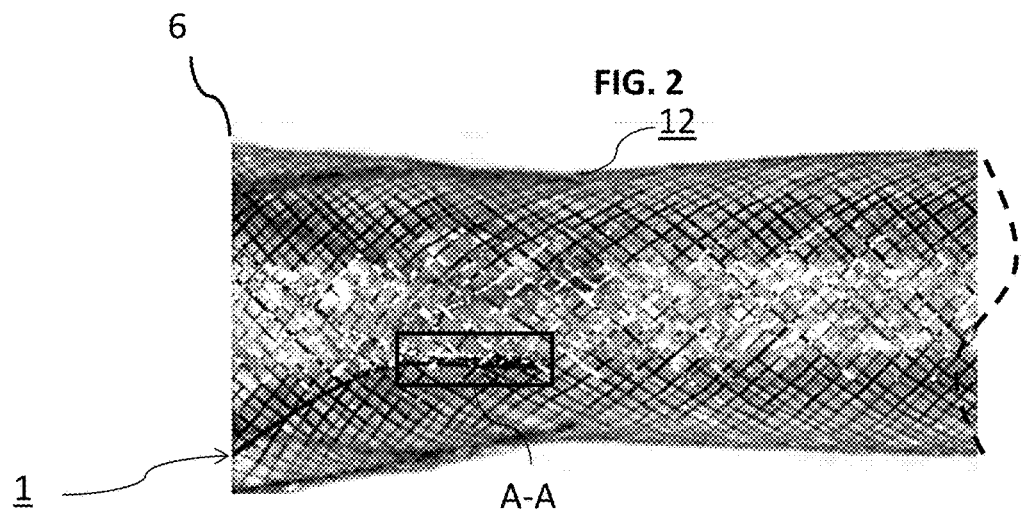
FIG. 2 depicts is another view of one embodiment of the herein disclosed expansion ring assembled with a tubular braided stent body.

In the following description, references are made to the accompanying drawings that form a part hereof and that show, by way of illustration, specific embodiments or examples. In referring to the drawings, like numerals represent like elements throughout the several figures. Turning to FIGS. 1 and 2, a side plan view of the herein disclosed ring 1 and corresponding support assemblies 10 is shown disposed at a proximal end 6 of body 12 which may be the later deployed end. FIG. 1 is a close up view of one embodiment of ring 1 when assembled with body 12 whereas FIG. 2 shows more of body 12 when an exemplary ring 1 is assembled with body 12. It is to be understood that body 12 may also include a distal end 8 (also known as an initially-deployed end) opposite its proximal end 6 as seen more clearly in FIG. 6, and ring 1 may be mechanically connected at distal end 8 and/or disposed at any positioned between ends 6 and 8.

As can be seen, body 12 of FIGS. 1 and 2 may be formed from a plurality of elongate members 22 braided or otherwise arranged to form a plurality of interstices 24. Members 22 may be formed from two or more metal wires, or polymeric fibers or strands of material. Ring 1 may be constructed from one or multiple interconnect support assemblies 10 that together form a frame of ring 1 that is capable of imparting one or more additive radial forces to an inner wall and/or an outer wall of lumen 20. In this regard, ring 1 may be selectively positioned and arranged for rapidly opening and/or maintaining body 12 in an opened position without having to weld, solder, glue, or otherwise connect ring 1 to body 12 itself.

Figure 3:
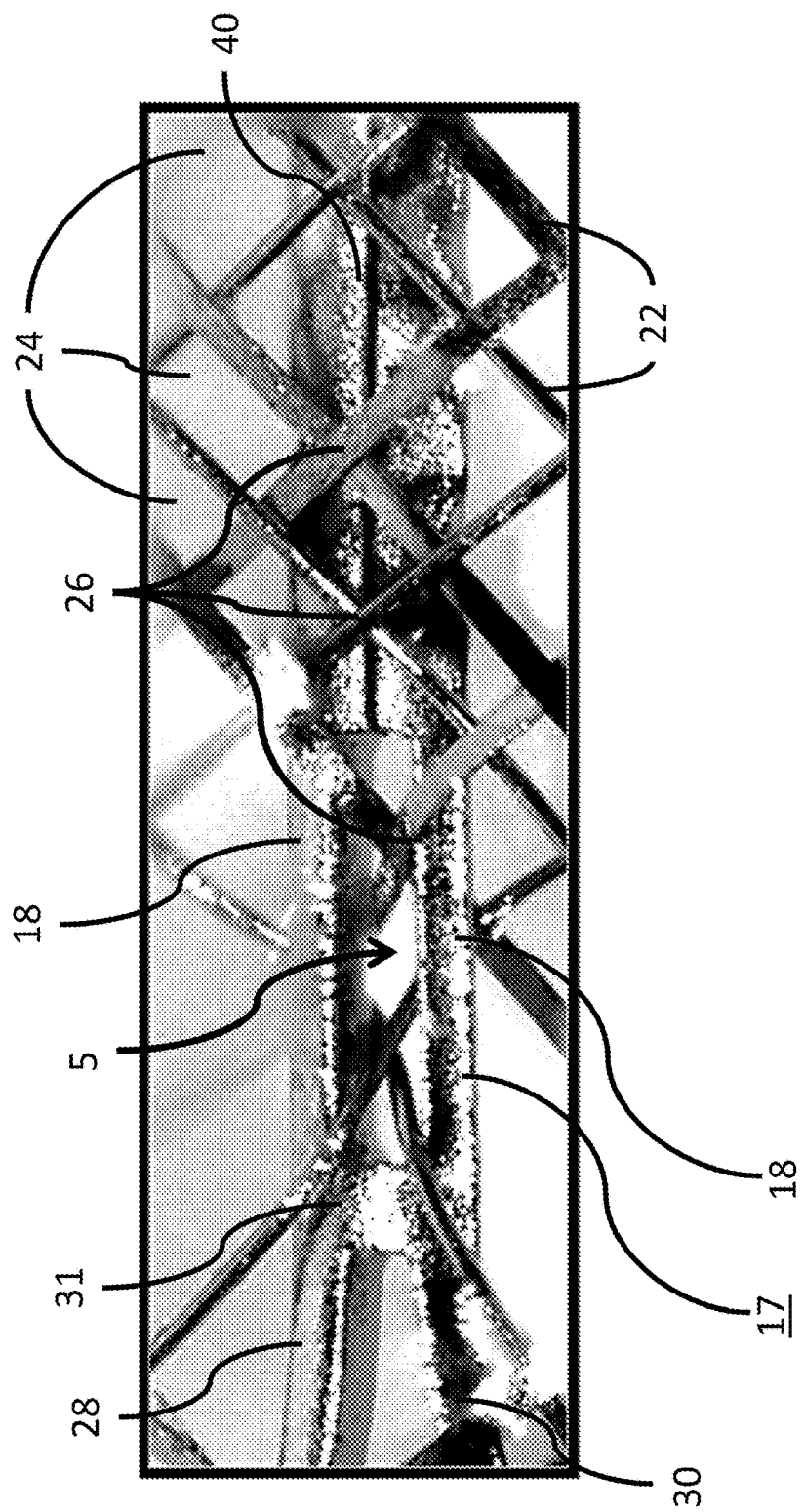
FIG. 3 is a close-up view of plane A-A of FIG. 2 showing certain features of the expansion ring assembled with the tubular braided stent body.

Turning to FIG. 3 is a close up view of plane A-A of FIG. 2 more clearly showing an exemplary claw 17 of one assembly 10 interlaced with the interstices 24 and braided, elongate members 22. As can be seen, assembly 10 may include a first leg 28 joined with a second leg 30 at a first intersection 31. While legs 28 and 30 are seen integrally formed with each other in FIG. 3, each assembly 10 is not so limited and legs 28 and 30 may be removably attached to each other through a fastener including a band, bolt, clamp, coupling, dowel, hook, latch, key, or the like. Legs 28 and 30 may also be adhered to each other or welded to form intersection 31. Additionally, if one or more fasteners are used in a particular implementation, they can be removably connected or welded, soldered, and/or crimped. Fasteners and/or legs 28 and 30 can be formed of a radiopaque metal, such as platinum or tantalum, or may be formed of a non-radiopaque material, such as stainless steel.

By adding claw 17 to the end of a crown of each assembly 10, each ring 1 is allowed to interlace with body 12 without a permanent or rigid attachment to body 12 such as welding, soldering or a chemical adhesive. Once the claw 17 is effectively interlaced and connected with the body 12 and the desired location, braided members 22 can also move independently from ring 1 which removes the adverse impact that a permanent or rigid attachment previously had on body 12 to fully expand when assembled with an expansion ring.

Intersection 31 may also include a rotatable and/or twistable coupling so that each assembly 10 of ring 1 is capable of flexing a predetermined amount when body 12 and ring 1 is in use. One or more elongate members 18 may extend from intersection 31 and terminate at a locking mechanism 40 opposite intersection 31 and legs 28 and 30. In the embodiment of FIG. 3, a plurality of elongate members 18 are shown substantially aligned and offset from each other while being joined at mechanism 40 to form a void 5 therebetween.

In order to mechanically attach to body 12, each claw 17 may have respective members passed through and/or interlaced with interstices 24 and members 22 and then joined at mechanism 40. In this regard, one or more multiple braided pairs 26 of members 22 may be arranged in or in connection with void 5 so that claw 17 may be mechanically attached to inner and outer portions of lumen 20. Mechanism 40 of FIG. 3 may be formed from a weld, crimp, band, clamp, or adhesive so that each of members 18 are fixedly attached to each other.

Figure 4A:
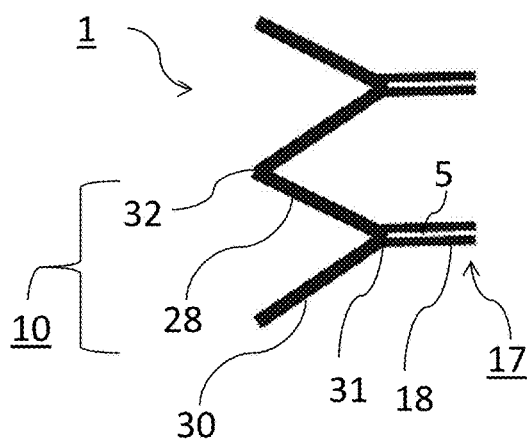
FIG. 4A is a side plan view of certain features of an exemplary expansion ring having support assemblies.
Figure 4C:
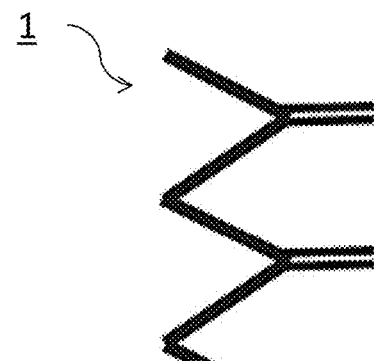
FIG. 4C is a side plan view of certain features of an exemplary expansion ring having support assemblies.
Figure 4B:
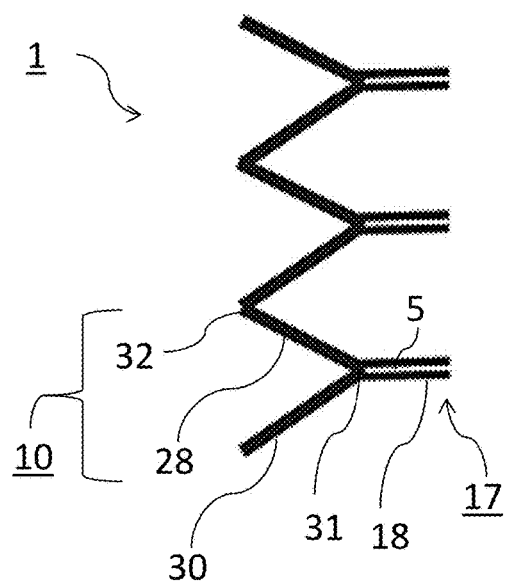
FIG. 4B is a side plan view of certain features of an exemplary expansion ring having support assemblies.

Turning to FIGS. 4A through 4C are depictions of rings 1 having multiple assemblies 10 though any number of assemblies 10 could be used as needed or required depending on need or preference. FIG. 4A specifically depicts two interconnected support assemblies 10 interconnected at a second intersection 32 with leg 28 extended therefrom towards intersection 31. FIG. 4B similarly depicts three interconnected assemblies 10 and FIG. 4C depicts four interconnected assemblies 10. It is to be understood assemblies 10 may be integrally formed with each other at intersection 32 or may be joined together using any of the herein described fasteners. It is to be understood that each assembly 10 can be a compression element capable of flexing a predetermined amount such that FIG. 4A depicts two compression elements, FIG. 4B depicts three compression elements, and FIG. 4C depicts four compression elements. In this respect, ring 1 with corresponding compression elements can move between a compressed configuration before deployment within the vasculature as well as a deployed configuration with a lumen 20 having a greater diameter than the compressed configuration. Additionally, legs 28 and 30 of each assembly 10 at intersections 31 and/or 32 may be formed as a V-shape as shown in FIGS. 4A through 4C with acute and/or oblique angles formed between legs 28 and 30. Optionally, instead of being V-shaped, legs 28 and 30 of each assembly 10 can be formed as "U" shaped, elliptical shaped, curved generally, loop or bight at the junction portion.

Figure 5B:
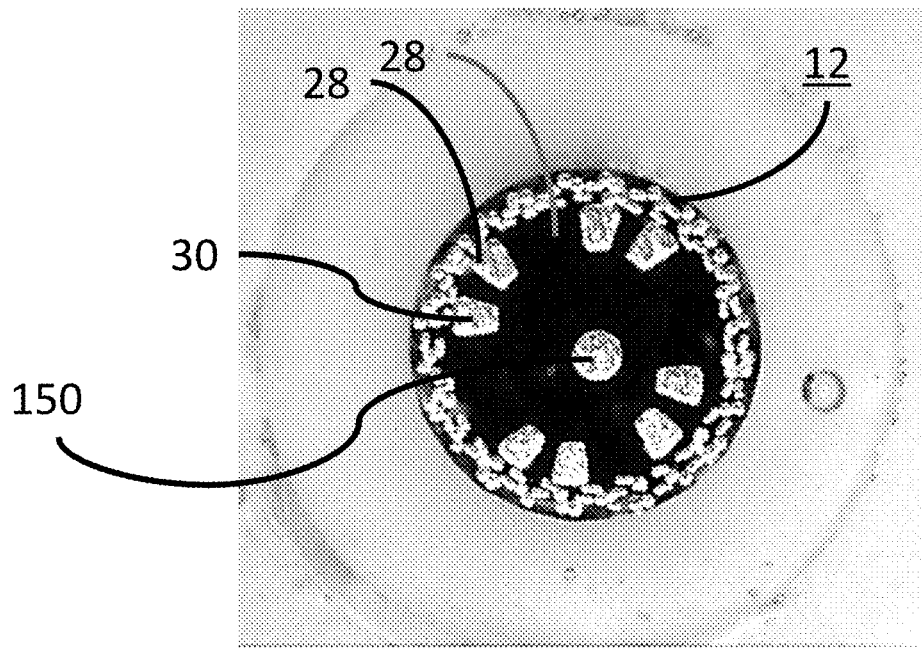
FIG. 5B is forward plan view of an example prototype of the exemplary expansion ring of FIG. 5A when assembled with a tubular braided stent body showing its inner lumen in a compressed state at a cross-section of the tubular braided stent body aft of the claw.
Figure 5C:
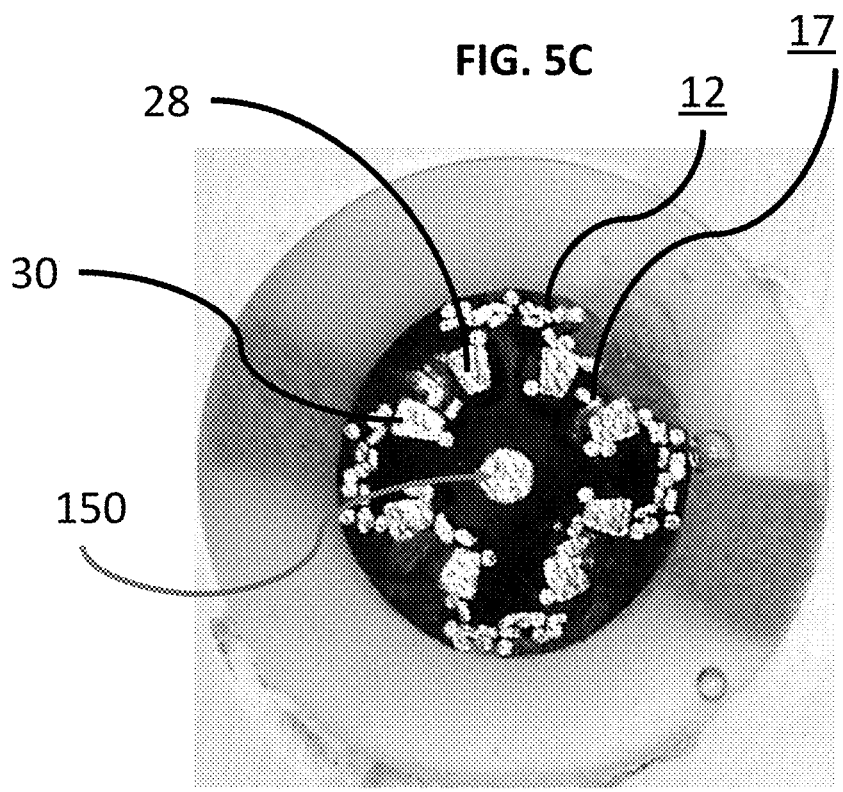
FIG. 5C is a forward plan view of the exemplary expansion ring of FIG. 5B when assembled with a tubular braided stent body showing its inner lumen in a compressed state at a cross-section of the claw.

Turning to FIG. 5A is a perspective view of exemplary ring 1 with a plurality of interconnected assemblies 10. While each assembly 10 may be V-shaped as in FIGS. 4A-4C, FIG. 5A depicts how each assembly 10 may be arranged in a bowed orientation. In this regard, legs 28 and/or 30 may include a curved or arched portion that bows with a predetermined resistance to compression. It is to be understood that each assembly 10 of ring 1 may have the same or a different resistance so that each ring 1 can be individualized for the specific vasculature implementation. FIG. 5B is a forward plan view of an example prototype of ring 1 of FIG. 5A when assembled with body 12 in a compressed state at a cross section of body 12 aft of claw 17 to show each of legs 28 and 30 and lumen 20 of body 12. A delivery mechanism 150 is depicted in lumen 20 for positioning and assembling each ring 1 with the inner and outer surfaces of body 20. Similarly, FIG. 5C a forward plan view of ring 1 of FIG. 5B when assembled with body 12 showing its inner lumen 20 in a compressed state at a cross-section of claw 17 with example delivery mechanism 50. As can be seen, in a compressed state each ring 1 is operable to assemble with inner and outer surfaces of body 12 while also providing outward expanding radial forces to the stent body to counter the inwardly applied compression in the compressed state.

Each assembly 10 and its constituent features may be formed of a superelastic material, such as a nickel-titanium alloy or Nitinol, or may be formed of a non-superelastic material, such as spring steel or MP35N, an alloy of 35% nickel, 35% cobalt, 20% chromium, and 10% molybdenum, by weight. Legs 28 and 30 of each assembly 10 may also be formed from a shape memory material having a shape memory position in the opened state.

Figure 6:
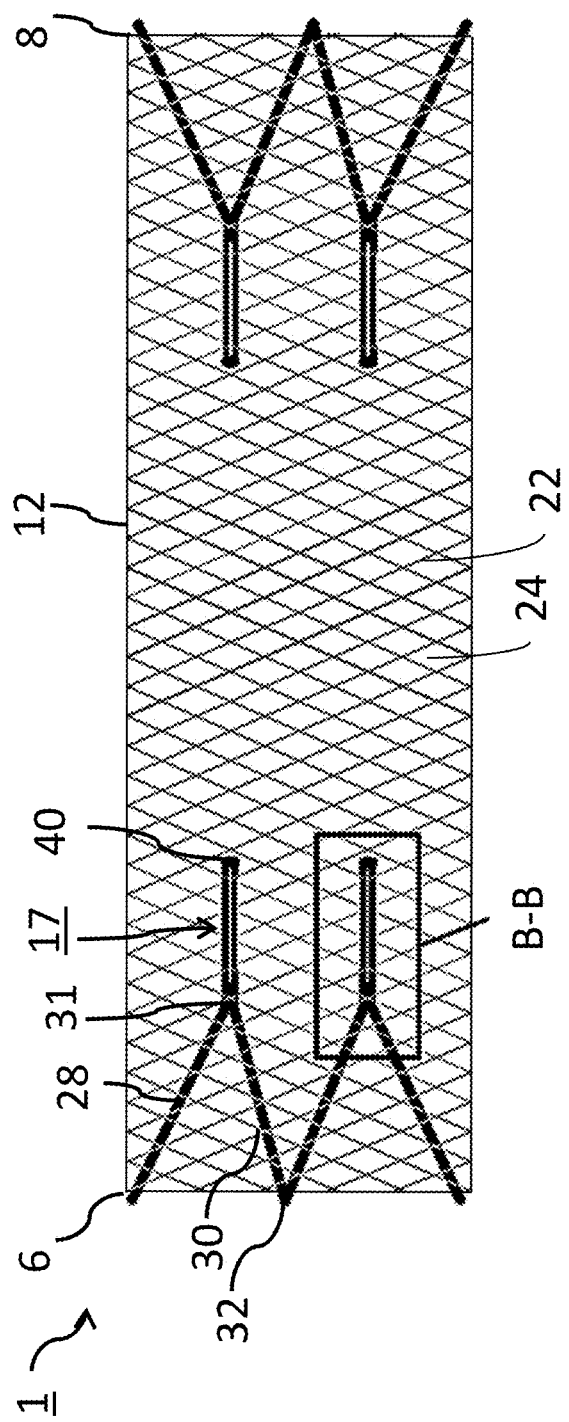
FIG. 6 depicts a side plan view of exemplary expansion rings having multiple claws when assembled at respective proximal and distal ends of a tubular braided stent body.

Turning to FIG. 6, a side plan view of rings 1 being assembled at both ends 6 and 8 of body 12 is shown. It can be seen that claw 17 of each assembly 10 is oriented to mechanically connect with braided members 22 of body 12 whereas opposing intersections 32 of each assembly 10 is in communication with ends 6 and 8, respectively. It also to be understood that intersection 32 of each assembly 10 formed from joined legs 28 and 30 may be mechanically connected to one or more members 22 and interstices 24 similar to claw 17. In this regard, legs 28 and 30 at intersection 32 do not need to directly attach to body 12, for example, by being welded or fastened directly to body 12 itself. Instead, similar to intersection 31, legs 28 and/or 30 can be directly joined together by being passed through one or more interstices 24 and interlaced with associated members 22, be joined together, and extend back towards respective intersections 31.

Figure 7:
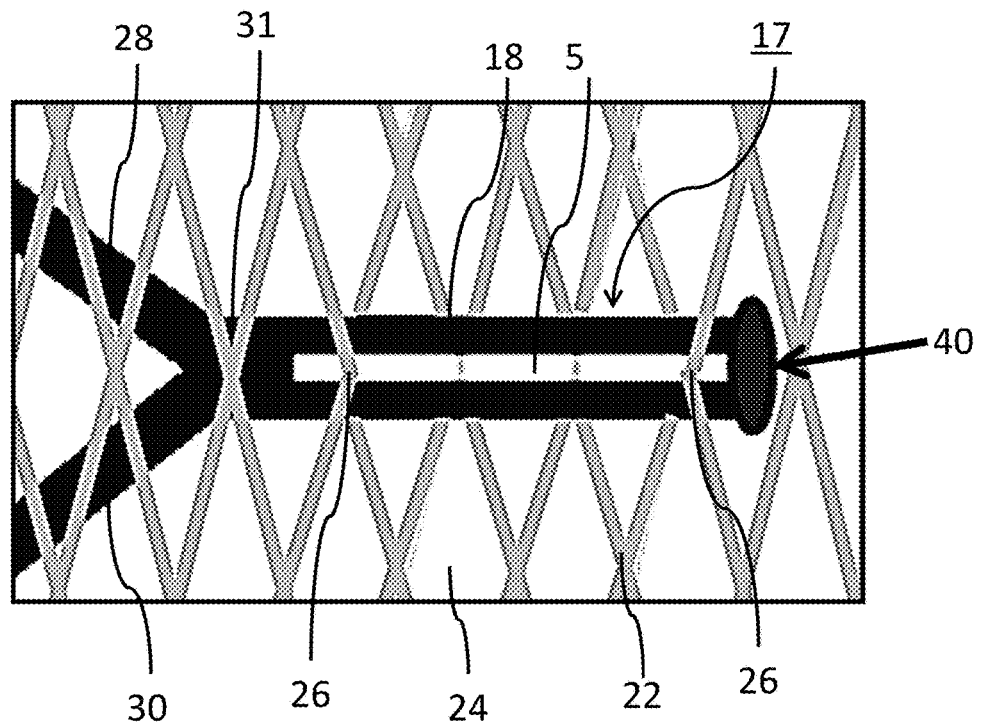
FIG. 7 is a close-up view of plane B-B of FIG. 6 showing certain features of one of the depicted expansion rings weaved through interstices of the tubular braided stent body with a fixed attachment.
Figure 9A:
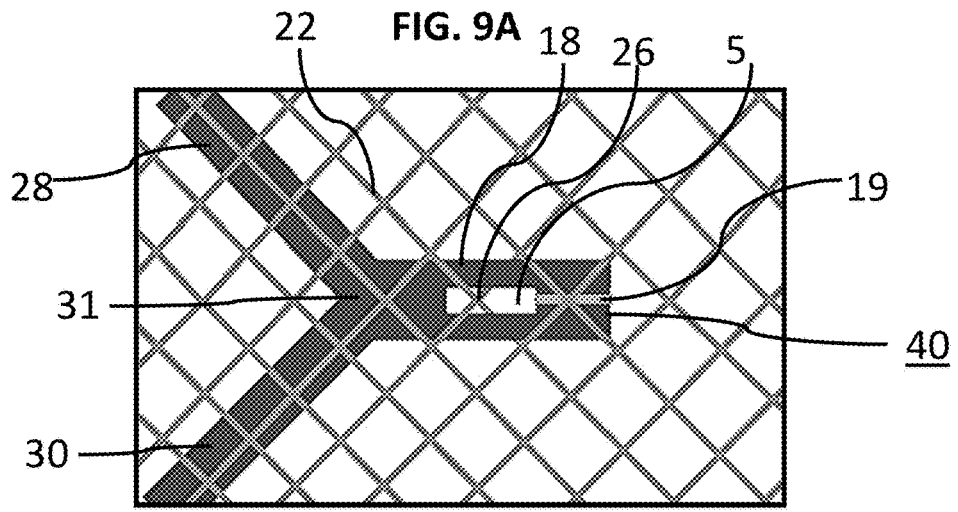
FIG. 9A depicts a side plan view of an exemplary expansion ring assembled with a tubular stent body, wherein a claw of the expansion ring is being secured using a single braid wire pair of the tubular stent body.
Figure 9B:
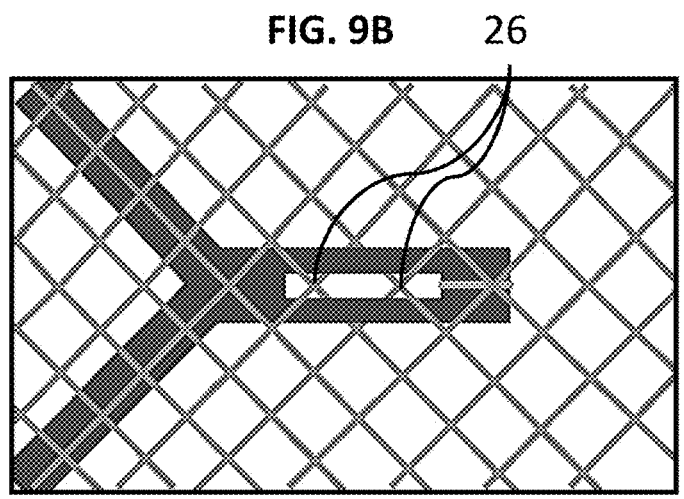
FIG. 9B depicts a side plan view of an exemplary expansion ring assembled with a tubular stent body, wherein a claw of the expansion ring is being secured using two braided wire pairs of the tubular stent body.
Figure 9C:
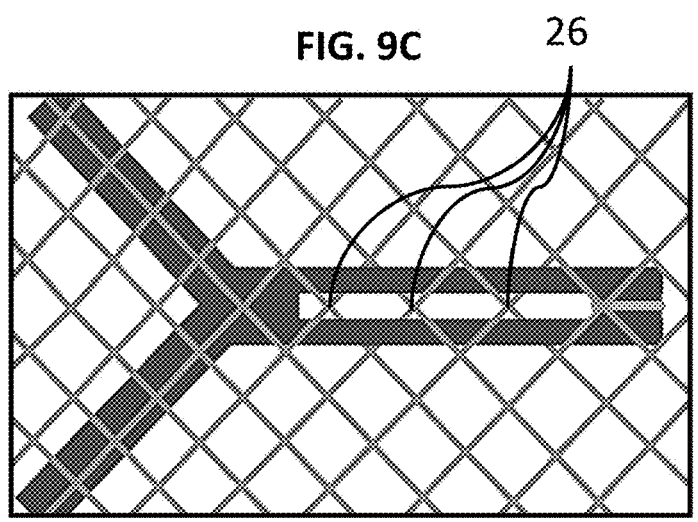
FIG. 9C depicts a side plan view of an exemplary expansion ring assembled with a tubular stent body, wherein a claw of the expansion ring is being secured using three braided wire pairs of the tubular stent body.

FIG. 7 depicts a close-up view of plane B-B of FIG. 6 depicting an exemplary claw 17 interlaced with members 22 and interstices 24. More specifically, legs 28 and 30 can be seen being joined together at intersection 31 with each of legs 28 and 30 disposed within lumen 20. After being joined at intersection 31, claw 17 may have a plurality of substantially aligned elongate members 18 that extend from intersection 31 towards mechanism 40 to form void 5. Mechanism 40 may include any of the previously described fasteners that join each of members 18 together or may be a weld, crimp, chemical adhesive, or the like. It can also be seen that two braided pairs 26 of members 22 pass through void 5 and are therefore interlaced with inner and outer portions of lumen 20 and members 24 of body 12. However, the herein disclosed solution is not so limiting and as shown in FIGS. 9A-9C, each member 18 and corresponding void 5 of claw 17 can be weaved with members 22 in a variety of ways. For example, only one braided pair 26 can interlaced with members 18 and void 5 of claw 17 (FIG. 9A), two braided pairs 26 can interlace with members 18 and void 5 of claw 17 (FIG. 9B), and/or three braided pairs 26 can interlace with members 18 and void 5 of claw 17 (FIG. 9C).

Members 18 of FIGS. 9A-9C may enter and exit braided pairs 26 at the same location along braided body 12.

FIG. 8 similarly depicts a side plan view of rings 1 being selectively positioned at ends 6 and 8 as well as ring 1 being disposed between ends 6 and 8 along a central portion of body 12. It is to be understood that the embodiment of FIG. 8 is not intended to be limiting and any number of rings 1 can be included between ends 6 and 8.

Turning to FIGS. 10A-10C, additional exemplary side plan views ring 1 assembled with body 12 are shown. Specifically, in FIG. 10A three braided pairs 26 are shown interlaced with void 5 and associated members 18, wherein portions of claw 17 are shown exiting and entering respective braided pairs 26 when claw 17 interlaces with braided body 12 and mechanically attaches thereto. In contrast, claws 17 of FIGS. 10B and 10C enter and exit at different locations of members 22 and interstices 24 than of FIG. 10A even when three braided pairs 26 are in communication with void 5.

Figure 11A:
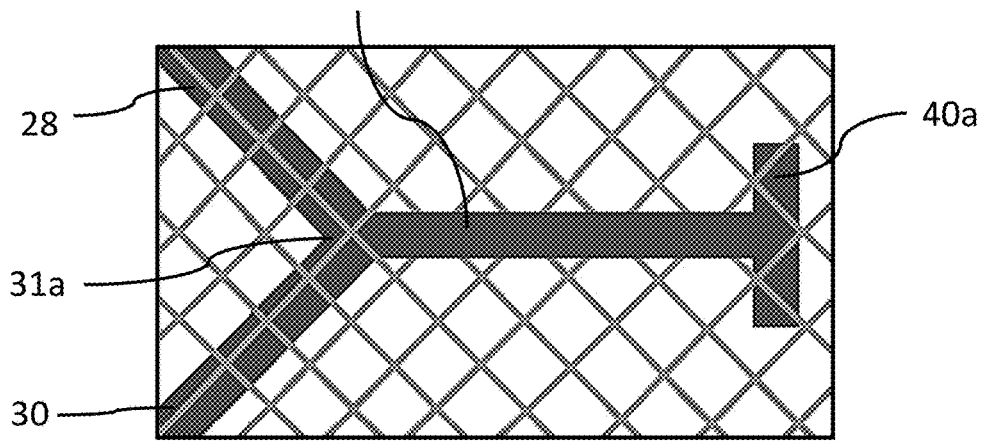
FIG. 11A depicts a close up side plan view of an exemplary expansion ring assembled with a tubular stent body depicting an embodiment having T-shaped endings.
Figure 11B:
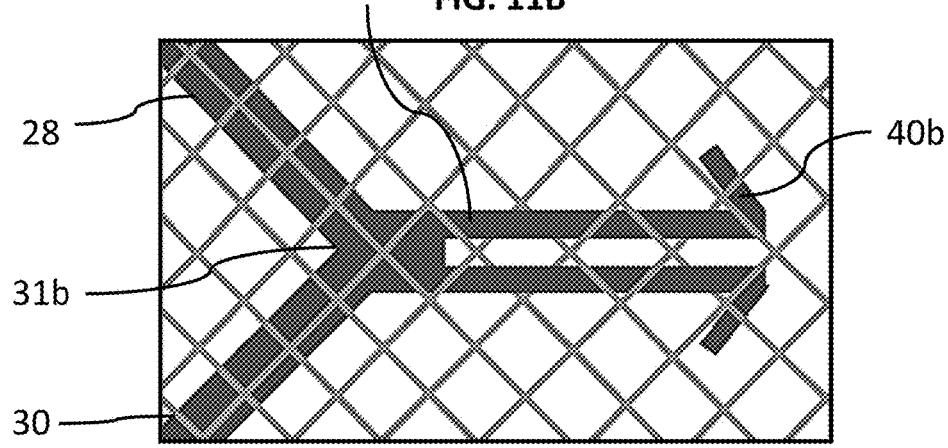
FIG. 11B depicts a close up side plan view of an exemplary expansion ring assembled with a tubular stent body depicting an embodiment having hook-shaped endings.

Alternative claw designs are also contemplated for use with assemblies 10 of ring 1. For example, in FIG. 11A, it can be seen that claw 17a can include only a single elongate member 18a extended from intersection 31a and terminating in a T-shaped locking mechanism 40a. In this embodiment, claw 17a can interlace with a braided pair 26 over intersection 31a, extend to an outer portion of body 12 until terminating in a T-shaped member of mechanism 40 that can interlace with multiple interstices 24 of body 12 to mechanically connect claw 17a to body 12. In another alternative embodiment of FIG. 11B, claw 17b can be seen with a plurality of elongate members 18b extended between intersection 31b and hooked-end locking mechanism 40b. Either or both of members 18b may interlace with members 22 and one or a plurality of braided pairs 26 and terminate in a hooked member of mechanism 40b. The hooked member of mechanism 40b may have an upwardly extended hooked portion operable to mechanically secure each member 18b to a braided pair 26. Both of mechanisms 40a and 40b may be used in place of welding, an adhesive, crimping, or a fastener of the previously disclosed mechanisms 40.

Figure 12A:
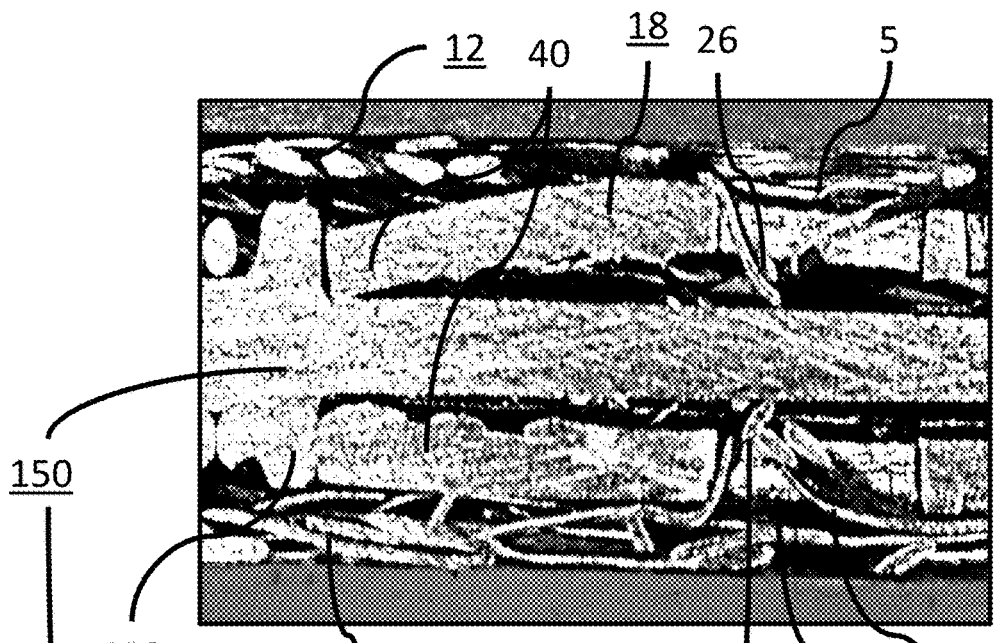
FIG. 12A depicts a side plan view an example prototype of one example ring assembled with a tubular stent body along a longitudinal cross section of a claw assembled with the tubular stent body.
Figure 12B:
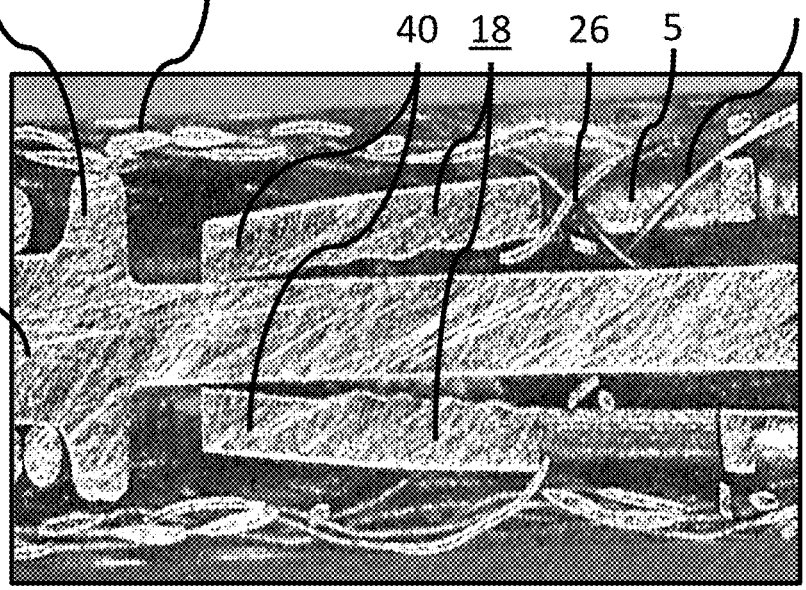
FIG. 12B depicts a side plan view of an example prototype of one example ring assembled with a tubular stent body along a longitudinal cross section of a claw assembled with the tubular stent body.

Turning to FIGS. 12A and 12B, each figure depicts side plan views prototypes of example claws 17 when assembled with body 12 along a longitudinal cross section of claw 17. As shown in each of FIGS. 12A and 12B, mechanism 150 and corresponding bump 152 can position member 18 and corresponding gap 5 with one or more members 22 and/or pairs 26. FIGS. 12A and 12B are not intended to be limiting and claw 17 and/or its constituent features may be assembled with body 12 with or without mechanism 150 as needed or desired.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A braided stent system, the system comprising:
    a stent body having a lumen formed by a plurality of braided members with interstices formed therebetween; and
    a first expansion ring connected to the stent body, the first expansion ring comprising a frame defined by a plurality of interconnected support assemblies selectively positioned to impart an outwardly expanding radial force to the stent body, each support assembly comprising:
    a plurality of legs joined at a first intersection and connected to one of the other interconnected support assemblies at a second intersection opposite the first intersection; and
    a claw portion mechanically connected to the stent body through one or more of the interstices of the stent body, wherein the claw portion mechanically connects the expansion ring to inner and outer portions of the stent body by being extended away from the first intersection, being interlaced through at least two of the interstices, and terminating at a locking mechanism opposite the first and second intersections;
    wherein at least one of the claw portions comprises a plurality of aligned elongate members extended between the first and second intersections and locking mechanisms to form a void through which the plurality of interstices pass.

2. The system of claim 1, wherein the plurality of legs of the frame are bowed causing the frame to be resistant to compression, the legs being twistable about the first and second intersections.

3. The system of claim 1, wherein the locking mechanism includes one of a T-shaped end or outwardly extending hooked members operable to fixedly connect to the interstices of the stent body.

4. The system of claim 1, wherein a plurality of pairs of the braided members passes through the void.

5. The system of claim 1, where the locking mechanism fixedly connects the expansion ring to the stent body by joining ends of the aligned elongate members opposite the first intersection through welding, soldering, crimping, or an adhesive bond.

6. The system of claim 1, where the locking mechanism fixedly connects the expansion ring to the stent body by joining ends of the aligned elongate members opposite the first intersection through a metallic band or ring.

7. The system of claim 1, wherein at least one of the second intersections forms at least one of a V-shape, a U-shape, or an elliptical curve.

8. The system of claim 1, wherein at least one of the first intersections forms V-shape, a U-shape, or an elliptical curve.

9. The system of claim 1, wherein the stent body includes a proximal end, a distal end, and a central portion disposed therebetween, and
    wherein the first expansion ring is disposed on or adjacent the distal or proximal ends of the stent body with the second intersections of the interconnected support assemblies being joined at or adjacent the other of the respective distal or proximal ends.

10. The system of claim 9, further comprising:
    a second expansion ring connected along the central portion of the stent body, the second expansion ring comprising a frame defined by a plurality of interconnected support assemblies selectively positioned to impart a balanced outwardly expanding radial force to the stent body, each support assembly comprising:

a plurality of legs joined at a first intersection and connected to one of the other interconnected support assemblies at a second intersection opposite the first intersection; and a claw portion mechanically connected to the stent body through one or more of the interstices of the stent body.

\* \* \* \* \*